United States Patent
Sendelbach et al.

(10) Patent No.: US 6,749,843 B2
(45) Date of Patent: Jun. 15, 2004

(54) COSMETIC COMPOSITIONS CONTAINING ELECTRICALLY CONDUCTIVE POLYMERS

(75) Inventors: Gerhard Sendelbach, Darmstadt (DE); Thomas Krause, Darmstadt (DE); Anja Duchscherer, Hadamar (DE)

(73) Assignee: Wella Aktiengesellschaft, Darmstadt (DE)

( * ) Notice: Subject to any disclaimer, the term of this patent is extended or adjusted under 35 U.S.C. 154(b) by 106 days.

(21) Appl. No.: 10/066,121

(22) Filed: Jan. 31, 2002

(65) Prior Publication Data
US 2002/0146442 A1 Oct. 10, 2002

(30) Foreign Application Priority Data
Feb. 6, 2001 (DE) .......................... 101 05 139

(51) Int. Cl.$^7$ .......................... A61K 31/74; A61K 7/00; A61K 7/06
(52) U.S. Cl. ................. 424/78.02; 424/70.1; 424/78.08; 424/400; 424/401
(58) Field of Search ................. 424/400, 401, 424/70.1, 78.02, 78.08

(56) References Cited

U.S. PATENT DOCUMENTS

| 5,338,541 A | 8/1994 | Matz |
| 5,989,874 A | * 11/1999 | Nakanishi et al. .......... 435/101 |

FOREIGN PATENT DOCUMENTS

| DE | 41 18 704 A1 | 12/1992 |
| DE | 196 31 563 A1 | 2/1998 |
| EP | 0 339 340 A2 | 11/1989 |
| EP | 0 411 689 A1 | 2/1991 |
| EP | 0 457 529 A1 | 11/1991 |
| EP | 0 539 123 A2 | 4/1993 |
| EP | 0 709 423 A1 | 5/1996 |
| FR | 2 704 554 | 11/1994 |
| FR | 2 707 493 | 1/1995 |
| FR | 2 709 954 | 3/1995 |
| FR | 2 722 687 | 1/1996 |
| GB | 2 207 153 A | 1/1989 |
| WO | WO 92/05761 | 4/1992 |
| WO | WO 01/12138 A1 | 2/2001 |
| WO | WO 01/12139 A1 | 2/2001 |

OTHER PUBLICATIONS

Schrader: "Grundlagen Und Rezepturen Der Kosmerika", 2. Auflage 1989, pp. 728–737.
Anonymous: "Performance in Cosmetics 2000", Internet, Online 2000, XP002235073, Mar. 17, 2003, pp. 1–2.
Anonymous: "Flexan 130" Internet, Online, XP0025074, Mar. 17, 2003,.
Anonymous: "Ormecon –Pure Polyaniline Later", Intaernet, Online Sep. 1995, XP002235080, Mar. 14, 2003.
Anonymous: "Ormecon –Polyaniline Powder Ormecon", Internet, Online, Sep. 1995, XP002235075, Mar. 14, 2003.
Anonymous: "Ormecon –A Conductive Polymer . . . " Internet, Online Aug. 1995, XP002235076, Mar. 14, 2003.
G. Pagani.: "Heterocycle–Based Electric Conductors", Heterocycles, vol. 37, N. 3, 1994, pp. 2069–2086.
Chimie Organique Moderne de Robert et Caserio, Heterocycles a Caractere Aromatique, Chapter 27, 1977, pp. 675–676.

* cited by examiner

Primary Examiner—Shelley A. Dodson
(74) Attorney, Agent, or Firm—Michael J. Striker

(57) ABSTRACT

A method of reducing the flyaway effect occurring during treatment of hair with a cosmetic composition is disclosed. According to this method an effective amount of an electrically conductive polymer is added to the cosmetic composition prior to treatment of the hair. Preferably the cosmetic composition is a shampoo or hair care composition, which contains from 0.001 to 5% of the electrically conductive polymer.

18 Claims, No Drawings

COSMETIC COMPOSITIONS CONTAINING ELECTRICALLY CONDUCTIVE POLYMERS

BACKGROUND OF THE INVENTION

The subject matter of the invention is a cosmetic composition containing an electrical conductive polymer. The composition especially is a hair treatment composition in the form of a shampoo or a hair care composition and reduces the flyaway effect when hair is treated with it.

Freshly washed hair, especially thin hair, is inclined to stand out from the head after drying because of an acquired static charge. This so-called flyaway effect is troublesome. Conventional solutions for this problem involve use of styling agents, such as hair sprays, hair fixing agents or foams, which however have the disadvantage that they fix the hair and limit the natural mobility of the hairstyle. One other solution is the use of quaternarized care materials, e.g. cationic surfactants or cationic polymers, which load the hair and lead to a reduction of the electrostatic charge. Conventional hair-conditioning preparations, such as rinse-off care compositions or leave-on care compositions, are usually formulated as aqueous emulsions. The essential ingredients include cation-active substances, such as cationic surfactants, hydrophobic substances, such as fatty alcohols, and other oily components, emulsifiers, and additional specific active ingredients and perfumes. The most important ingredients are cationic surfactants, fatty alcohols and emulsifiers. A review of the principal ingredients of care rinses and hair care compositions is given by Schrader, "Foundations and Compositions of Cosmetics (Grundlagen und Rezepturen der Kosmetika)", $2^{nd}$ Edition, 1989, pp. 728 to 737. The principal purposes of the conditioning agents are the improvement of the stylability, the combability, the luster and feel of the treated hair. The application of the cationic care ingredients to the hair however leads to a comparatively heavy burden or loading of the hair as well as the desired effect, because of the comparatively large amount of required care ingredients. Loading of the hair however leads immediately to negative styling properties, especially in the case of fine hair. The treated hair feels heavy and loaded, which is not always desirable.

SUMMARY OF THE INVENTION

It is an object of the present invention to provide a cosmetic composition, which has typical hair care properties and especially which reduces the flyaway effect.

It is an additional object of the present invention to provide a cosmetic composition, which at least reduces an impression of the treated hair being heavy and loaded in comparison to hair treated with the conventional hair care compositions.

It is a further object of the present invention to provide a cosmetic composition, which avoids impairing the mobility of the hairstyle in comparison to that obtained by treatment with a conventional styling composition.

It has been surprisingly found that these objects can be attained by cosmetic compositions comprising an electrically conductive polymer.

According to the invention the cosmetic composition contains at least one electrically conductive polymer in a suitable cosmetic foundation.

In order to avoid the above-described flyaway effect without the troublesome side effects obtained by using conventional styling and care ingredients and to reduce the static charge, new intrinsically conductive polymers are used. By applying the hair treatment compositions according to the invention, which contain these polymers, the flyaway effect can be avoided. These polymers are known from other fields of art different from the cosmetic arts. They are used for treatment of surfaces, in order to avoid static charges, e.g. on electronic components or photographic films. They are applied by conventional application methods, such as spraying, pressing or brushing, among others. It has now been found that they may also be worked into a hair treatment composition without difficulty. In the treated hair the flyaway effect is clearly reduced. Only very small amounts of the conductive polymer are required and the hair feels light and not loaded in comparison to the result of treating with a conventional hair care product.

Intrinsically conductive polymers are usually ethylenically unsaturated and conjugated, whereby charge transport is possible in the polymer molecule. This type of polymer is also called an organic metal. They have a conductivity of at least $10^{-5}$, preferably of at least $10^{-2}$, especially preferably at least 1, siemens/cm. Suitable intrinsically electrically conductive polymers include, for example, polymeric compounds based on polyaniline, polyanisidine, polydiphenylamine, polyacetylene, polythiophene, polythioprene, polythienylvinylene, bithiophene, polypyrrole and polycroconaine and its derivatives. This sort of polymer is frequently made electrically conductive by doping. The doping can occur chemically or electrochemically. The polymeric compounds are partially oxidized by treatment with an oxidizing agent, such as iodine, sodium peroxydisulfate or bromine or other strong acids and are thus made electrically conductive. Other polymers could be made electrically conductive by partial reduction with a reducing agent. These methods are generally known in the art. The manufacture of intrinsically conductive polyaniline and polypyrrole is described, for example, in EP 0 539 123. Suitable polymer compounds are, e.g., polyradical cations. For increased stability of the formulation it is recommended that the polyradical cations be used in combination polymeric anionic compounds (polyanions) and that the composition does not contain any additional cationic substances, which compete for the counter ions and lead to failures.

The preferred conductive polymeric compounds are conductive polythiophenes, especially conductive polyalkylenedioxythiophene. These polymeric compounds are made by methods described in DE 41 18 704 and EP 0 339 340. 3,4-polyethylenedioxythiophene is especially preferred as the electrically conductive polymeric compound. A suitable commercially available product is Baytron® P of Bayer, an aqueous dispersion with 0.5% by weight of 3,4-polyethylenedioxythiophene (DEPT) and 0.8% by weight polystyrenesulfonate (PSS). Other preferred intrinsically electrically conductive polymers include conductive polyaniline, e.g. Versicon® (Allied Signal), a polyaniline with a conductivity of 2 to 4 S/cm or Ormecon® (Zipperling Kessler & Co.).

The cosmetic compositions according to the invention contain from 0.001 to 5 percent by weight, preferably 0.01 to 1 percent by weight, especially preferably from 0.02 to 0.5 percent by weight, of at least one intrinsically electrically conductive polymer, based on a total amount of the cosmetic composition present.

The cosmetic composition according to the invention is preferably an aqueous or aqueous/alcoholic composition. Lower alcohols suitable for cosmetic purposes having from one to four carbon atoms, e.g. ethanol and isopropanol, are preferred as the alcohols in the aqueous/alcoholic compositions of the invention. The aqueous or aqueous/alcoholic compositions according to the invention contain preferably from 40 to 95 percent by weight, especially preferably from 60 to 90 percent by weight, water. The alcohol content in the composition according to the invention is preferably from 1 to 30, especially preferably from 5 to 20, percent by weight. Also other water-soluble solvents or moisturizing agents, especially multivalent alcohols having from 2 to 4 carbon atoms, such as glycerol, ethylene glycols or propylene glycols, can be included in the cosmetic compositions according to the invention in an amount of from 0.1 to 10 percent by weight, preferably from 0.5 to 5 percent by weight.

At least one non-conductive film-forming synthetic or natural polymer can be contained in the compositions according to the invention in order to fix the electrically conductive polymeric compound on the hair. This additional polymer advantageously has nonionic, anionic or amphoteric character. Cationic polymers can be incompatible with Baytron® P. The additional non-conductive film-forming polymer is preferably present in an amount of from 0.5 to 10 percent by weight. Film-forming polymers are those polymers, which, when applied to the hair in an 0.1 to 5 percent by weight aqueous, alcoholic or aqueous-alcoholic solution are in a position to deposit a polymer film on the hair.

The composition according to the invention can also contain conventional cosmetic additive ingredients, e.g. perfume oils in an amount of preferably from 0.01 to 5 percent by weight; wetting agents or emulsifiers in an amount of preferably from 0.01 to 10 percent by weight; moisturizers; preservatives; bactericidal and fungicidal active-ingredients, such as 2,4,4-trichloro-2-hydroxy-diphenylether, parabene or methylchloroisothiazolinone, in an amount of from 0.01 to 1.0 percent by weight; buffer substances, such as sodium citrate or sodium phosphate, in an amount of form 0.1 to 1.0 percent by weigyht; dye substances, such as fluorescein sodium salt, in an amount of about 0.1 to 1.0 percent by weight; care ingredients, e.g. vegetable extracts, plant extracts, protein hydrolyzates, silk hydrolyzates, lanolin derivatives, in an amount of from 0.1 to 5 percent by weight; light-protective agents, anti-oxidants, radical trapping agents, anti-flaking agents, fatty alcohol, luster-imparting agents, vitamins and de-fatting agents, in an amount of from 0.01 to 10 percent by weight.

The composition according to the invention can have a pH in a pH range of from 2.0 to 9.5, preferably from 4.5 to less than 7 and especially preferably from 5.5 to 6.5. When the composition according to the invention is acidic or in the acid pH range, it can contain organic or inorganic acids, such as formic acid, tartaric acid, malic acid, maleic acid, fumaric acid, glyoxalic acid, pyrrolidone carboxylic acid, citric acid, lactic acid, sulfuric acid, acetic acid, hydrochloric acid, phosphoric acid, among others.

The composition according to the invention can be in the form of a lotion, an aerosol spray containing a propellant, a non-aerosol spray, an aerosol foam containing a propellant, a non-aerosol foam, a gel, a cream, an O/W emulsion, a W/O emulsion or a shampoo, in which the electrically conductive polymer is dissolved or dispersed. When the composition according to the invention has a low viscosity, it is particularly easily and satisfactorily distributed on the hair, also by spraying. The hair treatment composition according to the invention may then be combined with a suitable mechanically operated spraying device. By mechanically operated spraying device we mean those devices, which can produce a spray without using a propellant. Suitable mechanical spraying devices can, for example, include spray pumps or an elastic container provided with a spray valve, in which the composition according to the invention is filled under pressure. The composition according to the invention is dispensed from this latter elastic container by opening the spray valve because the elastic container contracts.

Hair and body cleansing compositions containing the electrically conductive polymer of the invention and at least one wash-active surfactant in an aqueous base are preferred embodiments of the invention. All those surfactants included for this purpose in shampoos or shower gels usually can be used as the wash-active surfactants. The surfactants can be present, alone or in a mixture, and are contained in an amount of preferable from 1 to 50 percent by weight, especially preferably from 1 to 30 percent by weight. Nonionic surfactants, amphoteric surfactants, zwitterionic surfactants and anionic surfactants are generally suitable.

Suitable anionic surfactants include, e.g. alkaline or alkaline earth salts of the $C_{10}$- to $C_{18}$-alkyl sulfates, the $C_{10}$- to $C_{18}$-alkyl sulfonates, the $C_{10}$- to $C_{18}$-alkyl benzyl sulfonates, the $C_{10}$- to $C_{18}$-xylyl sulfonates, the $C_{10}$- to $C_{18}$-alkyl sulfonates ethoxylated with from 1 to 10 ethylene oxide units, alpha-olefin sulfonates, sulfosuccinates, the ethoxylated sulfosuccinic acid semiesters of the general formula R—(OCH$_2$CH$_2$)$_m$—O$_2$C—CH$_2$—CH(SO$_3$M)—COOM, wherein R is a $C_{10}$- to $C_{18}$-alkyl group, M is an alkali or alkaline earth cation and m is a number from 1 to 10, especially sulfosuccinates, such as disodium laureth-3 sulfosuccinate, disodium PEG-5 lauryl citrate sulfosuccinate, disodium ricinolamido MEA-sulfosuccinate or disodium laurylamido MEA-sulfosuccinate and alkyl ether carboxylates of the general formula R—(OCH$_2$CH$_2$)$_n$—OCH$_2$—COOM, wherein R is a $C_{10}$- to $C_{18}$-alkyl group, M is an alkali or alkaline earth cation and n is a number from 1 to 10, especially sodium laureth-6 carboxylate or sodium laureth-11 carboxylate. Preferably at least one alkali and alkaline earth salt of $C_{10}$- to $C_{18}$-alkyl ether sulfate ethoxylated with from 1 to 10 ethylene oxide units is present in the hair cleansing compositions of the invention.

Suitable nonionic surfactants include e.g. alkoxylated fatty alcohols with a high degree of alkoxylation, e.g. from 11 to 50, and alkoxylated fatty acid esters, alkoxylated partial glycerides of branched or unbranched, saturated or unsaturated $C_6$- to $C_{20}$-fatty acids, and with an alkoxylation degree of 11 to 400, e.g. polyethylene glycol (200) glyceryl palmitate, alkoxylated polyol esters, such as ethoxylated sugar esters, for example polyethylene glycol(120)methyl glucose dioleate and alkylpolyglucosides, such as coconut glucosides, lauryl gluycosides or decylglucosides. For example, ethoxylated lauryl alcohol, tetradecyl alcohol, cetyl alcohol, oleyl alcohol or stearyl alcohol, which are used alone or in mixtures with each other, as well as fatty alcohols of ethoxylated lanolin, are suitable as fatty alcohol ethoxylates. Examples of the fatty acid ester ethoxylates include, above all, castor oil ethoxylated with 25 ethylene oxide units with the INCI name PEG-25 hydrogenated castor oil, castor oil ethoxylated with 35 ethylene oxide units with the INCI name PEG-35 castor oil and castor oil ethoxylated with 40 ethylene oxide units with the INCI name PEG-40 hydrogenated castor oil. Furthermore the ethoxylated fatty acid sugar esters known as nonionic surfactants, especially ethoxylated sorbitan fatty acid ester, but not ethyoxylated surfactants in general, are suitable for use in the cosmetic preparations according to the invention. The suitable ethoxylated fatty acid sugar esters include those marketed under the trade names Tween® and Arlacel® by ICI surfactants and the alkyl-polyglycosides, which are marketed under the trade neames Plantaren® or Plantacare® by Henkel or under the trade name Oramix® by Seppic.

Suitable amphoteric surfactants include for example betaines, such as cocoamidopropylbetaine or lauryl betaine, sulfobetaines, such as cocoamidopropyl hydroxysultaine, glycinates, such as cocoamphoglycinate (INCI-name: sodium cocoamphoacetate) and diglycinates and propionates, such as cocoampho-propionate.

Additional preferred embodiments according to the invention are hair conditioning compositions and of course both rinse-out hair care compositions (Rinses, Treatments) and also leave-on hair products (leave-in products). These hair care compositions are usually based on O/W emulsions and contain water, at least one hydrophobic ingredient (especially at least one fatty alcohol) and a suitable emulsifier besides the intrinsically electrically conductive polymer compound.

The amount of hydrophobic material in the composition depends on the requirements for the end product that is prepared. Hair care compositions, for example, can contain from 5 to 30 percent by weight and hair cremes can contain up to about 50 percent by weight. The hydrophobic material in the oil phase of the hair care emulsions may be selected from the group consisting of water-insoluble waxes, fatty materials or oily materials. These ingredients can be liquid or solid at room temperature. Suitable waxes or waxy materials includes e.g. natural renewable waxes (insect, animal and plant waxes), fossil waxes (oil wax, brown coal wax, peat wax or ozokerite), synthetic waxes (Fischer-Tropsch wax, polyethylene wax or amide wax), high-melting paraffins, esters, fats, long-chain carboxylic acids or long-chain $C_{10}$- to $C_{22}$-alcohols. Also oil or oily materials, such as naturally occurring, renewable oils (plant oils or vegetable oils), synthetic oils, silicone oils, mineral oils, volatile oils, water-insoluble branched or linear aliphatic hydrocarbon material, linear or branched alcohols, especially liquid fatty alcohols and long-chain ethers or esters, wherein the above-named substances preferably have at least eight carbon atoms. Suitable hydrocarbon materials include, e.g., liquid paraffins, squalane or squalene. Furthermore esters of divalent and multivalent alcohols are suitable, especially plant triglycerides, such as olive oil, almond oil, peanut oil, sunflower seed oil and synthetic triglycerides, such as $C_8$- to $C_{10}$-trifatty acid glycerol esters or also jojoba oil. Suitable hydrophobic substances for the compositions according to the invention also include mono- or diesters of the formula $R^1$—$COOR^2$, $R^1$—$COO$—$R^3OOR^1$ and $R^2$—$COO$—$R^3$—$COOR^2$, wherein $R^1$ represents a $C_8$- to $C_{22}$-alkyl group, $R^2$ represents a $C_3$- to $C_{22}$-alkyl group and $R^3$ represents a $C_2$- to $C_{16}$-alkyl groups. Naturally occurring monoesters or wax ester mixtures, e.g. present in jojoba oil or sperm oil, and branched primary alcohols, such as those known under the name guerbetaalcohols, are also suitable. The suitable hydrophobic substances also include additional substances, which are generally used in cosmetic compositions as turbidity inducing agents, especially those of formula $R^1$—$COO$—$(CHR^4CHR^5O)_n$—$COR^6$, wherein $R^1$ represents a $C_8$- to $C_{22}$-alkyl group, $R^4$ and $R^5$ represent hydrogen or methyl and $R^6$ represents hydrogen or $R^1$ and n is a number between 1 and 12, preferably 1, 2, 3 or 4. Ethylene glycol fatty acid diester or polyethylene glycol fatty acid diester present in solid form at room temperature is preferred.

The emulsion-form hair care composition according to the invention contains emulsifiers in an amount of from 0.5 to 30 percent by weight of the finished composition. Nonionic and anionic emulsifiers are suitable. Suitable emulsifiers include, for example, those described in "International Cosmetic Ingredient Dictionary and Handbook", 7th Edition, Volume 2, in the section "Surfactants", especially in the sub-section "Surfactants—Emulsifying Agents". Suitable nonionic emulsifiers include the above-named nonionic surfactants, especially ethoxylated fatty alcohols, ethoxylated nonylphenols, alkylpolyglycosides, fatty acid monoglycerides and diglycerides, ethoxylated and hydrogenated or non-hydrogenated castor oil, fatty acid alkanol amides and ethoxylated fatty acid esters. Suitable anionic emulsifiers can also be selected from the above-described anionic surfactants.

The conditioning composition according to the invention is employed in a method comprising distributing an amount sufficient for the desired conditioning effect in or on the wet or dry hair. The amount used depends on the abundance of the hair and usually amounts to from 1 to 25 g. In the preferred embodiment, the rinse product, the composition is rinsed out of the hair after an acting time of from 1 to 15 minutes. Subsequently the hair is thoroughly combed and shaped in a hairstyle. The hair is dried. Embodiments of this conditioning composition, which are leave-in products, are not rinsed out of the hair.

The following examples should illustrate the subject matter of the invention.

EXAMPLES

Example 1

Shampoos with Intrinsically Conductive 3,4-Polyethylene-dioxythiophene

| Raw Material | A, % | B, % | C, % | D, % | E, % | F, % | G, % |
|---|---|---|---|---|---|---|---|
| Texapon ® N28 Benz[1] | 35.0 | 35.0 | 35.0 | 35.0 | 35.0 | 35.0 | 35.0 |
| Baytron ® P[2] | — | 1.0 | 3.0 | 5.0 | 10.0 | 15.0 | 20.0 |
| Sodium Chloride | 4.0 | 4.0 | 4.0 | 4.0 | 4.0 | 4.0 | 4.0 |
| Dist. Water | To 100 | To 100 | To 100 | To 100 | To 100 | To 100 | To 100 |

[1]sodium laureth sulfate, 28% in water, preserved with benzoic acid
[2]aqueous dispersion of 0.5% of 3,4-polyethylendioxythiophene and 1.3% polystyrene sulfonate.

To test the flyaway effect wigged heads were washed in a half side test. A half head is washed with 6 ml shampoo (for about 1 min) and subsequently rinsed again with warm water (about 5 min). The wigged head is first dried with a hand towel and after that with hand hair drier. Prior to testing the flyaway effect the wigged head is conditioned for two days in a climate room at 20° C. and 65% relative humidity. The hair is combed with a nylon brush. The prevention of the flyaway effect by addition of the 5% Baytron® P (0.025% 3,4-polyethylenedioxythiophene) is clearly observable.

Example 2

Hair Care Compositions with Intrinsically Conductive 3,4-Polyethylene-dioxythiophene

| Raw Material | Sample A, % | Sample B, % | Sample C, % |
|---|---|---|---|
| Cetearyl alcohol | 1.5 | 1.5 | 1.5 |
| PPG-12-PEG-65 Lanolin Oil | 1.2 | 1.2 | 1.2 |
| Vaseline ® | 1.5 | 1.5 | 1.5 |
| Sodium cetearyl Sulfate | 0.6 | 0.6 | 0.6 |
| Sorbitol | 3.5 | 3.5 | 3.5 |
| Citric acid | 0.2 | 0.2 | 0.2 |

-continued

| Raw Material | Sample A, % | Sample B, % | Sample C, % |
| --- | --- | --- | --- |
| Ethanol | 12.0 | 12.0 | 12.0 |
| Baytron ® P | — | 5.0 | 10.0 |
| Water, dist. | To 100% | To 100% | To 100% |

To test the flyaway effect wigged heads were washed in a half side test. One half head is treated with 10 ml hair care composition A (acting time about 2 min) and subsequently rinsed again with warm water (about 5 min). The other half head is treated with hair care composition B or C. The wigged head is first dried with a hand towel and after that with hand hair drier. Prior to testing the flyaway effect the wigged head is conditioned for two days in a climate room at 20° C. and 30% relative humidity. The hair is combed with a nylon brush. The addition Baytron® P has a definite positive effect. The hair has little static charge.

All percentages are percentages by weight unless otherwise indicated.

The disclosure in German Patent Application 101 05 139.5-41 of Feb. 2, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in electrically conductive polymers in cosmetic compositions, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A cosmetic composition, comprising at least one electrically conductive polymer in a cosmetic foundation.

2. The cosmetic composition as defined in claim 1, wherein said at least one electrically conductive polymer has an electrical conductivity of $10^{-5}$ S/cm.

3. The cosmetic composition as defined in claim 1, wherein the at least one electrically conductive polymer is selected from the group consisting of polyaniline, polyanisidine, polyacetylene, polydiphenylamine, polyacetylene, polythioprene, polythienylvinylene, polythiophene, polycroconaine and polypyrrole.

4. The cosmetic composition as defined in claim 1, wherein the at least one electrically conductive polymer is a polyradical cation.

5. The cosmetic composition as defined in claim 4, wherein said polyradical cation is combined with a polyanion.

6. A cosmetic composition, comprising a cosmetic foundation and at least one electrically conductive polymer in said cosmetic foundation, wherein the at least one electrically conductive polymer is an electrically conductive 3,4-polyethylenedioxythiophene or an electrically conductive polyaniline.

7. A cosmetic composition, comprising a cosmetic foundation and at least one electrically conductive polymer in said cosmetic foundation, wherein the at least one electrically conductive polymer is a combination of an electrically conductive 3,4-poly-ethylenedioxythiophene and polystyrene sulfonate.

8. The cosmetic composition as defined in claim 1, containing from 0.001 to 5 percent by weight of the at least one electrically conductive polymer.

9. The cosmetic composition as defined in claim 1, in the form of a lotion, an aerosol spray, a non-aerosol spray, an aerosol foam, a non-aerosol foam, a gel, a cream, an O/W emulsion, a W/O emulsion or a shampoo.

10. The cosmetic composition as defined in claim 1, wherein the at least one electrically conductive polymer is dispersed or dissolved.

11. An aqueous hair or body cleansing composition, comprising at least one electrically conductive polymer, at least one wash-active surfactant and an aqueous base.

12. The aqueous hair or body cleansing composition as defined in claim 11, consisting of an O/W emulsion.

13. A method of treating hair, said method comprising the steps of:
a) providing a cosmetic composition comprising an effective amount of at least one electrical conductive polymer and a cosmetic foundation therefor;
b) applying the cosmetic composition to the hair to be treated in a sufficient amount for the treating; and
c) after the applying, allowing the cosmetic composition to act on the hair for a predetermined time interval.

14. A method of at least reducing flyaway effect of hair treated with a cosmetic composition, said method comprising the step of adding an effective amount of at least one electrically conductive polymer to said cosmetic composition prior to treating the hair with the cosmetic composition.

15. The method as defined in claim 13 or 14, wherein said cosmetic composition contains from 0.001 to 5% by weight of at least one polymer compound selected from the group consisting of electrically conductive polyaniline, electrically conductive polyanisidine, electrically conductive polyacetylene, electrically conductive polydiphenylamine, electrically conductive polyacetylene, electrically conductive polythioprene, electrically conductive polythienylvinylene, electrically conductive polythiophene, electrically conductive polycroconaine and electrically conductive polypyrrole.

16. The method as defined in claim 13 or 14, wherein said cosmetic composition contains from 0.01 to 5% by weight of 3,4-polyethylene-dioxythiophene.

17. A method of treating hair, said method comprising the steps of:
a) providing a cosmetic composition comprising an effective amount of a combination of an electrically conductive 3,4-polyethylenedioxythiophene and polystyrene sulfonate in a cosmetic foundation;
b) applying the cosmetic composition to the hair to be treated in a sufficient amount for the treating; and
c) after the applying, allowing the cosmetic composition to act on the hair for a predetermined time interval.

18. A method of at least reducing flyaway effect of hair treated with a cosmetic composition, said method comprising the step of adding an effective amount of a combination of an electrically conductive 3,4-polyethylene-dioxythiophene and polystyrene sulfonate to said cosmetic composition prior to treating the hair with the cosmetic composition.

* * * * *